United States Patent
Bendlin

(10) Patent No.: US 7,072,106 B2
(45) Date of Patent: Jul. 4, 2006

(54) DEVICE FOR MARKING MICROSCOPIC PREPARATIONS

(75) Inventor: Cornelia Bendlin, Goettingen (DE)

(73) Assignee: Carl Zeiss Jena GmbH, Jena (DE)

(*) Notice: Subject to any disclaimer, the term of this patent is extended or adjusted under 35 U.S.C. 154(b) by 0 days.

(21) Appl. No.: 10/482,355

(22) PCT Filed: May 18, 2002

(86) PCT No.: PCT/EP02/05526

§ 371 (c)(1),
(2), (4) Date: Aug. 11, 2004

(87) PCT Pub. No.: WO03/005098

PCT Pub. Date: Jan. 16, 2003

(65) Prior Publication Data

US 2004/0257647 A1    Dec. 23, 2004

(30) Foreign Application Priority Data

Jun. 29, 2001 (DE) .................. 101 31 564

(51) Int. Cl.
*G02B 21/00* (2006.01)
*G02B 21/34* (2006.01)

(52) U.S. Cl. ...................... 359/396; 359/368
(58) Field of Classification Search .......... 359/368, 359/391, 396, 397

See application file for complete search history.

(56) References Cited

U.S. PATENT DOCUMENTS

| 1,129,742 A | 2/1915 | Sheaff |
| 3,827,777 A | 8/1974 | Ford |
| 3,912,360 A | 10/1975 | Beckel |
| 4,262,426 A * | 4/1981 | Miyazaki .................. 359/368 |
| 4,690,521 A | 9/1987 | Saccomanno |
| 4,807,979 A | 2/1989 | Saccomanno et al. |
| 5,076,679 A * | 12/1991 | Hervas ...................... 359/381 |
| 5,715,082 A | 2/1998 | Saccomanno et al. |

FOREIGN PATENT DOCUMENTS

| DE | 203 650 | 10/1983 |
| DE | 40 11 575 | 10/1990 |

OTHER PUBLICATIONS

Patent Abstracts of Japan, vol. 006, No. 018 (p-100), 56-140314 Nov. 2, 1981, Olympus Optical Co., Ltd.
Patent Abstracts of Japan, vol. 1997, No. 07, 09-073033 Mar. 18, 1997, Olympus Optical Co., Ltd.
Patent Abstracts of Japan, vol. 1997, No. 11, 09-179032 Jul. 11, 1997, Olympus Optical Co., Ltd.

* cited by examiner

*Primary Examiner*—Mark A. Robinson
(74) *Attorney, Agent, or Firm*—Reed Smith LLP

(57) ABSTRACT

The invention is directed to a device for marking microscopic preparations. It is characterized in that arc-shaped marks can be applied to a preparation in a simple, ergonomic manner by means of writing tips. For this purpose, the writing tips are lowered onto the preparation and the writing movement is carried out by means of an individual operating element.

4 Claims, 3 Drawing Sheets

DEVICE FOR MARKING MICROSCOPIC PREPARATIONS

CROSS-REFERENCE TO RELATED APPLICATIONS

This application claims priority of PCT Application Ser. No. PCT/EP02/05526. filed May 18, 2002 and German Application No. 101 31 564.3, filed Jun. 29, 2001, the complete disclosures of which are hereby incorporated by reference.

BACKGROUND OF THE INVENTION a) Field of the Invention

The invention is directed to a device for marking microscopic preparations. It can be used in connection with a conventional optical light microscope. Above all, in pathological anatomy, hematology, cytology and microbiology, it is often desirable to permanently mark determined parts of the microscopic preparation so as to make it easier to find these parts again quickly. However, the object of actual relevance should not be concealed or overlaid by the mark.

b) Description of the Related Art

To this end, devices have been developed in which a writing tip is fastened to one of the objectives in such a way that when the objective approaches the preparation or when the preparation is moved toward the objective the writing tip leaves a mark on the microscopic preparation in the vicinity of the optical axis of the objective. Such devices are known, for example, from U.S. Pat. No. 4,690,521, U.S. Pat. No. 4,807,979 and U.S. Pat. No. 5,715,082. The basic disadvantage in these marking devices is the space required for the mechanical construction between the objective and the preparation, which space is generally larger than the observation distance of the objective, so that the objective can not be used to observe the preparation. Since one of the objectives is therefore not available for use, it has been suggested to design a marking device in such a way that it can be screwed into the objective turret of the microscope in place of an objective. This kind of solution is described in DE-OS 40 11 575. In so doing, a felt tip which is held in the interior of the marking device is lowered manually onto the preparation and leaves a circular mark in the manner of a stamp. The disadvantage of this solution consists in that the size and shape of the mark is determined by the stamp; that is, different marks can not be applied for different labeling of different locations in the preparation.

OBJECT AND SUMMARY OF THE INVENTION

Proceeding from these disadvantages of the prior art, it is the primary object of the invention to provide a marking device for microscopic preparations which makes it possible to apply marks of different shapes and sizes to the preparation in a simple, ergonomic manner.

This object is met, according to the invention, in a device for marking microscopic preparations comprising an ink reservoir which is screwed into an objective turret in place of a microscope objective having an optical axis. At least one writing tip is provided which is connected with the reservoir and the writing tip is adapted to being lowered onto the preparation outside of the optical axis substantially parallel to the optical axis and being rotatable substantially around the optical axis.

In this connection, it is advantageous to provide a plurality of writing tips which are rotatable jointly around the optical axis in order to generate different patterns for marking such as whole circles and arcs of circles of different lengths as well as punctiform marks. Also, the size of the marks can be varied by varying the distance of the writing tips from the axis of rotation.

An especially ergonomic solution is given by providing means which automatically convert the movement for lowering the writing tips onto the preparation into a rotating movement of the writing tips around their axis of rotation. A conversion of this kind is realized by means of a first substantially tubular carrier which can be locked at the objective turret and which has at least two slit-shaped cutouts in its circumferential surface, a second substantially tubular carrier located coaxially in the interior of the first carrier, wherein the second carrier is rotatable and axially displaceable relative to the first carrier, is connected with the writing tips and the ink reservoir or ink reservoirs and has at least two groove-shaped cutouts in its circumferential surface; further, a preferably annular portion is provided which encloses the first carrier in such a way that it is movable along the wall of the first carrier and is supported against the first carrier by a spring, wherein the slits of the first carrier and the grooves of the second carrier are inclined relative to one another and are oriented with respect to one another in such a way that pin-shaped connection elements located in the interior of the annular portion engage in the grooves through the slits in such a way that when the annular portion moves axially in the direction of the preparation the second carrier is carried along by means of the connection elements and when this entraining movement is arrested due to the writing tips striking against the microscopic preparation the second carrier is rotated relative to the first carrier and the writing tips accordingly produce circular, arc-shaped or approximately punctiform marks on the preparation.

In a particularly advantageous construction of the arrangement, the slits in the first carrier extend parallel to the optical axis and the grooves of the second carrier are constructed as a helical groove. In this case, to apply the mark, the annular portion is guided straight downward through the pins acting as drivers, and the second carrier and accordingly the writing tips are carried along until the writing tips meet the preparation. Since a further downward movement of the writing tips is not possible, the continued movement of the annular portion is transformed by the engagement of the pins in the helical groove into a rotating movement of the second carrier and accordingly of the writing tips. The length of the applied circular arcs is determined by the movement of the circular part after the writing tips meet the preparation. Since a circular mark is applied to the preparation without the user having to execute a rotating movement, the solution according to the invention is particularly ergonomic.

Various diameters of the marks can be achieved by arranging the writing tips in the second carrier in such a way that their distance from the axis of rotation can be changed. The distance can be adjusted, for example, in that the writing tips are arranged eccentrically at cylindrical ink reservoirs and the ink reservoirs are rotated in a coupled manner by suitable means such as toothed wheels, toothed rims or friction wheels.

BRIEF DESCRIPTION OF THE DRAWINGS

The invention will be described in the following with reference to a preferred embodiment form.

The marking device is shown in partial section on the drawings for purposes of illustration.

DESCRIPTION OF THE PREFERRED EMBODIMENTS

Figure 1:
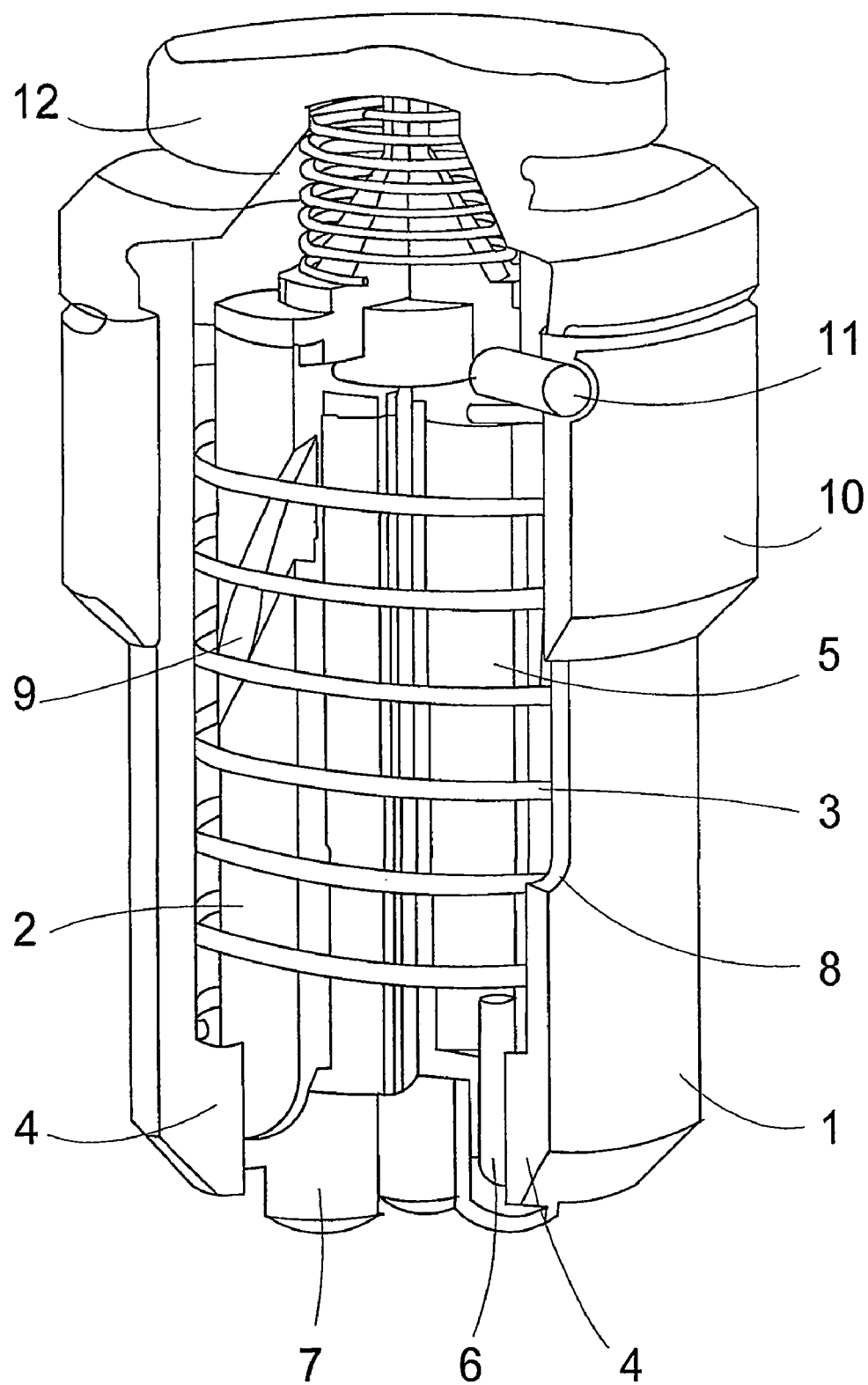
FIG. 1 shows a marking device according to the invention in the rest position.

In FIG. 1, a first, outer cylindrical carrier 1 encloses a second, inner carrier 2 which is supported by a spring 3 against a collar 4 of the outer carrier 1. Three ink reservoirs 5 with writing tips 6 are located in the inner carrier 2. When the marking device is not in use, the writing tips are covered by protective caps 7. The outer carrier 1 has a plurality of vertical slits 8, only one of which is shown in the drawing. The inner carrier 2 has the same quantity of helical grooves 9. An annular portion 10 encloses the outer carrier 1 and serves as an actuating element. For this purpose, the annular portion 10 engages in the helical grooves 9 through the slits 8 by means of pin-shaped connection elements 11. The inner carrier 2 is rotatable as well as displaceable axially relative to the outer carrier 1, while the annular portion 10 is only movable axially relative to the carrier 1 due to the vertical slits 8. In its upper part 12, the outer carrier 1 has a thread, not shown, for screwing into an objective eye of an objective turret of a microscope.

Figure 2:
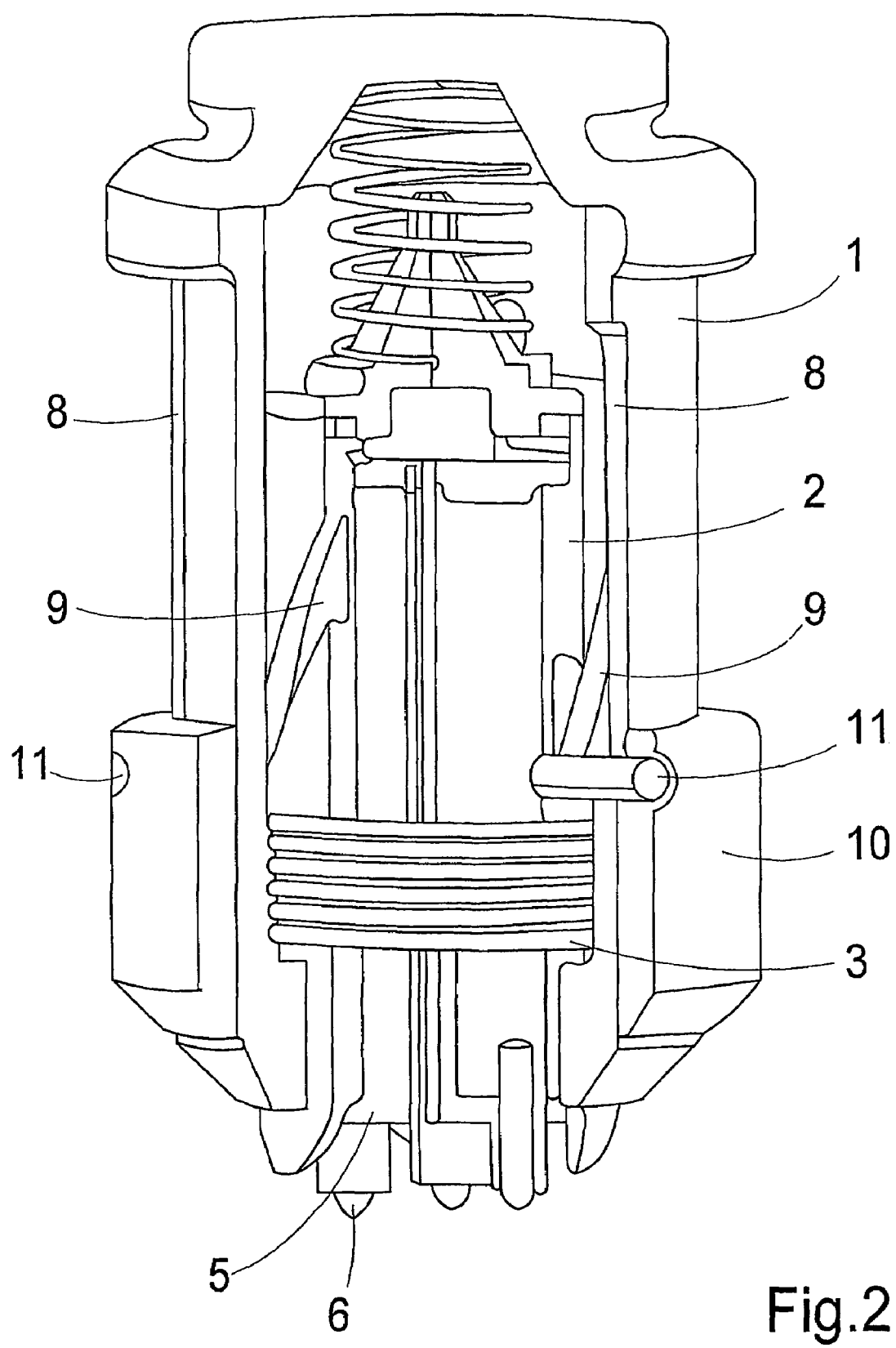
FIG. 2 shows the same marking device in the actuated state.

FIG. 2 shows the marking device after actuation. The annular portion 10 was moved downward manually so as to be guided by the slits 8 of the outer carrier 1. The inner carrier 2 is carried along by means of the pins 11 and is likewise pushed downward out of the carrier 1 and the writing tips 6 are moved toward the preparation, not shown.

Figure 3:
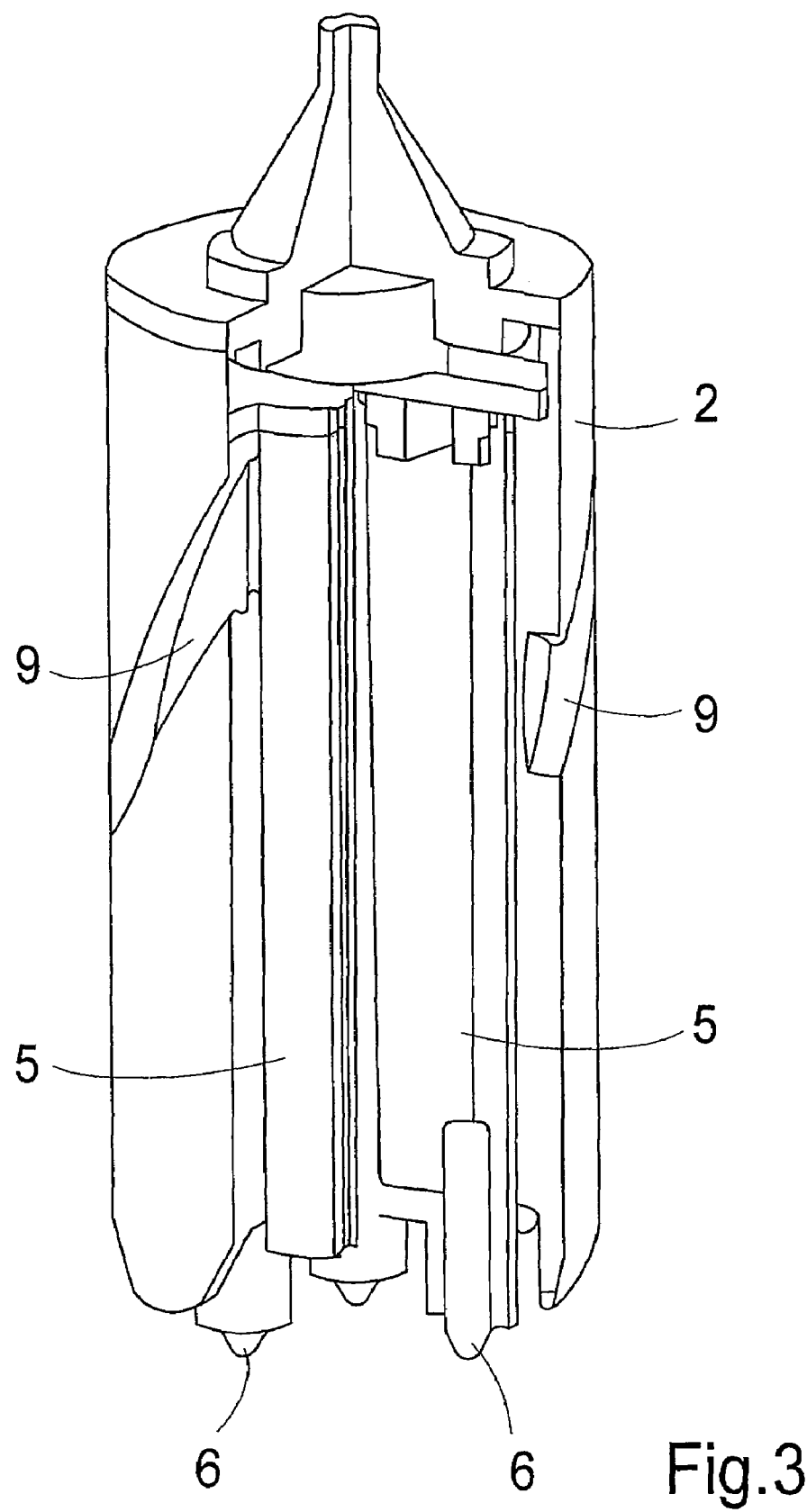
FIG. 3 is a better view of the second carrier as individual part.

For better illustration, the inner carrier 2 is shown in FIG. 3 without the outer carrier 1. In its circumference, the carrier 2 has a quantity of helical grooves 9 corresponding to the quantity of slits 8 of the outer carrier 1. The ink reservoirs 5 with the writing tips 6 are arranged in its interior. All of the writing tips 6 have the same distance from the axis of rotation of the inner carrier 2. When the ink reservoirs 5 are cylindrical and the writing tips 6 are arranged eccentric to the cylinder axis of the ink reservoirs 5, the distance of the writing tips from the axis of rotation of the inner carrier 2 can be adjusted in a simple manner by rotating the ink reservoirs jointly about their respective axis, e.g., with knurled wheels.

To apply a mark on a microscopic preparation, the appropriate location is identified with an observation objective of the microscope and the marking device located in another eye of the objective turret is then swiveled in. The allocation of the optical axis, and accordingly of the marking device, with respect to the location on the preparation to be marked is obtained by adjusting the objective turret and objectives in a suitable manner. Naturally, the position of the preparation may not be changed in doing so. Subsequently, the actuating ring 10 is moved down toward the preparation. The inner carrier 2 is then carried along by the pins 11 and the writing tips 6 are accordingly lowered onto the preparation. When the writing tips meet the preparation, the downward movement of the inner carrier 2 is arrested. When the actuating ring 10 is moved down farther, the pins 11 cause a rotational movement of the carrier 2 around its axis coinciding with the optical axis of the microscope by means of the helical grooves 9 of the inner carrier 2 and therefore cause a circular movement of the writing tips 6 on the preparation. Accordingly, the applied marks are circular arcs whose length depends upon the distance by which the actuating ring 10 continues to move after the writing tips 6 have met the preparation. When fully actuated, a circle can also be applied. When the actuating ring is released, the spring 3 presses the inner carrier 2 back into the starting position again.

The invention is not limited to the embodiment example shown herein. Accordingly, means can also be provided for applying circular arcs of defined length, for example. In the same way, the invention can be used to apply marks on the preparation (e.g., Petri dishes) from below in an inverted microscope.

While the foregoing description and following drawings represent the present invention, it will be obvious to those skilled in the art that various changes may be made therein without departing from the true spirit and scope of the present invention.

The invention claimed is:

1. A device for marking microscopic preparations which is screwed into an objective turret in place of a microscope objective having an optical axis, comprising:
   an ink reservoir;
   at least one writing tip being provided which is connected with the ink reservoir; and
   said writing tip adapted to being lowered into the preparation outside of the optical axis substantially parallel to the optical axis and being rotatable substantially around the optical axis,
   wherein means are provided for converting the movement for lowering the writing tip onto the preparation into a rotational movement of the writing tip around the axis of rotation.

2. The device for marking microscopic preparations according to claim 1, wherein a first substantially tubular carrier is provided which can be locked at the objective turret, wherein at least two slit-shaped cutouts are provided in its circumferential surface, wherein a second substantially tubular carrier is provided in the interior of the first carrier coaxial to the first carrier, wherein the second carrier is rotatable and axially displaceable relative to the first carrier, wherein the second carrier is fixedly connected with the writing tips and the ink reservoir so as to be exchangeable, wherein the second carrier has at least two groove-shaped cutouts in its circumferential surface, wherein the slits of the first carrier and the grooves of the second carrier are inclined relative to one another and are oriented with respect to one another in such a way that a penetration space is formed between a groove of an inner circumferential surface and a slit of an outer circumferential surface, wherein an annular portion is provided which encloses the first carrier in such a way that it is movable along the wall of the first carrier and is supported against the first carrier by a spring, and wherein the annular portion has at least two pin-shaped connection elements in the interior which engage in the penetration space of the grooves of the inner circumferential surface and the slits of the outer circumferential surface in such a way that when the annular portion moves in the axial direction the second carrier is carried along by this movement and when this entraining movement is arrested due to the writing tips meeting the microscopic preparation the second carrier is rotated relative to the first carrier.

3. The device for marking microscopic preparations according to claim 2, wherein the slit-shaped cutouts in the circumferential surface of the first carrier extend parallel to the optical axis.

4. The device for marking microscopic preparations according to claim 2, wherein the groove-shaped recesses of the second carrier are constructed as helical grooves.

* * * * *